United States Patent
Fessmann et al.

(10) Patent No.: US 6,939,382 B2
(45) Date of Patent: Sep. 6, 2005

(54) 4, 5-DIAMINOPYRAZOLE DERIVATIVES IN DIMER FORM, AND USE THEREOF IN THE OXIDATION DYEING OF KERATIN FIBRES

(75) Inventors: Thilo Fessmann, Aulnay solus Bois (FR); Eric Terranova, Magaganosc (FR)

(73) Assignee: L'Oreal S.A., Paris (FR)

( * ) Notice: Subject to any disclaimer, the term of this patent is extended or adjusted under 35 U.S.C. 154(b) by 145 days.

(21) Appl. No.: 10/336,856

(22) Filed: Jan. 6, 2003

(65) Prior Publication Data

US 2004/0107511 A1 Jun. 10, 2004

Related U.S. Application Data

(60) Provisional application No. 60/346,970, filed on Jan. 11, 2002.

(30) Foreign Application Priority Data

Jan. 4, 2002 (FR) .............................. 02 00098

(51) Int. Cl.$^7$ ................................. A61K 7/13
(52) U.S. Cl. ....................... 8/405; 8/405; 8/406; 8/409; 8/410; 8/411; 8/412; 8/423; 8/570; 8/573; 548/302.7
(58) Field of Search ........................... 8/405, 406, 409, 8/410, 411, 412, 423, 570, 573; 548/302.7

(56) References Cited

U.S. PATENT DOCUMENTS

| 5,061,289 A | | 10/1991 | Clausen et al. ................. 8/405 |
| 5,718,731 A | * | 2/1998 | Loewe et al. ................... 8/409 |
| 6,099,592 A | | 8/2000 | Vidal et al. ..................... 8/409 |
| 6,338,741 B1 | | 1/2002 | Vidal et al. ..................... 8/409 |
| 6,716,257 B2 | * | 4/2004 | Goettel et al. ................. 8/409 |

FOREIGN PATENT DOCUMENTS

| EP | 0 375 977 | 2/1994 |
| EP | 0 740 931 | 8/1997 |
| EP | 1 236 460 | 9/2002 |
| WO | WO 02/066919 | 9/2002 |
| WO | WO 02/069918 | 9/2002 |

OTHER PUBLICATIONS

English language Derwent Abstract of WO 02/069918.
English language Derwent Abstract of WO 02/069919.
English language Derwent Abstract of WO 1 236 460.

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

The present, invention relates to novel 4,5-diaminopyrazole derivatives, to a composition for the oxidation dyeing of keratin fibers, and in particular of human keratin fibers, comprising, as oxidation base, at least one such derivative, and also to an oxidation dyeing process using this composition.

25 Claims, No Drawings

4, 5-DIAMINOPYRAZOLE DERIVATIVES IN DIMER FORM, AND USE THEREOF IN THE OXIDATION DYEING OF KERATIN FIBRES

The present invention relates to novel 4,5-diaminopyrazole derivatives, to a composition for the oxidation dyeing of keratin fibres, and in particular of human keratin fibres, comprising, as oxidation base, at least one such derivative, and also to an oxidation dyeing process using this composition.

It is known practice to dye keratin fibres, and in particular human hair, with dye compositions containing oxidation dye precursors, which are generally known as oxidation bases. These oxidation bases are colourless or weakly coloured compounds that, when combined with oxidizing products, may give rise to coloured compounds and dyes by a process of oxidative condensation. These oxidation bases are generally ortho- or para-phenylenediamines, ortho- or para-aminophenols and heterocyclic compounds such as pyrazole or pyrazolopyrimidine derivatives.

It is also known that the shades obtained with these oxidation bases may be varied by combining them with coloration modifiers, also known as couplers, the said couplers being chosen especially from aromatic meta-diamines, meta-aminophenols, meta-diphenols and certain heterocyclic compounds.

The variety of molecules used as oxidation bases and couplers allows a wide range of colours to be obtained.

The "permanent" coloration obtained by means of these oxidation dyes must moreover satisfy a certain number of requirements. Thus, it must have no toxicological drawbacks, it must allow shades to be obtained in the desired intensity and it must show good fastness to external agents (light, bad weather, washing, permanent-waving, perspiration and rubbing).

The colorants must also make it possible to cover white hairs and, finally, they must be as unselective as possible, i.e. they must produce the smallest possible coloration differences along the same length of keratin fibre, which may in fact be differently sensitized (i.e. damaged) between its end and its root. They must also show good chemical stability in the formulations and must have a good toxicological profile.

Furthermore, for a certain number of applications, dyes that give chromatic shades on the hair are desired.

It is already known practice, for example in patent application EP 375 977, to use 4,5-diaminopyrazole derivatives in oxidation dyeing for the dyeing of keratin fibres. Patent applications EP 873 109, EP 871 426 and EP 692 245 also disclose compositions for oxidation dyeing comprising diaminopyrazole derivatives and couplers of the meta-phenylenediamine, meta-aminophenol or benzoxazine type.

However, these compositions do not make it possible to satisfy all the above requirements.

The aim of the present invention is to develop novel dye compositions that produce colours in the red range and that do not have the drawbacks of the dyes of the prior art. In particular, the aim of the invention is to develop powerful, particularly chromatic and bright colorations, which are relatively unselective and which have excellent fastness properties with respect to the various attacking factors to which keratin fibres may be subjected.

To this end, one subject of the present invention is novel 4,5-diaminopyrazole derivatives corresponding to formula (I) below:

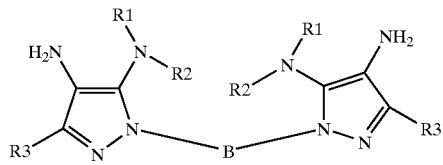

in which

R$_1$ to R$_3$, independently, represent a hydrogen; a linear or branched alkyl or alkenyl radical which may be substituted with one or more groups chosen from OR, NRR', SR, SOR, SO$_2$R, COOR, CONRR', PO(OH)$_2$ and SO$_3$X, a cationic or non-cationic heterocycle, an aryl or a halogen atom; R$_1$ with R$_2$ may form a heterocycle containing at least 4 atoms including the nitrogen atom to which they are attached;

R$_3$ also represents an alkoxy, amino, alkylamino or dialkylamino radical;

B is a linear or branched, saturated or unsaturated C$_1$–C$_{14}$ hydrocarbon-based chain, which may contain one or more double or triple bonds and which may be substituted with one or more groups chosen from OR, NRR', SR, SOR, SO$_2$R, COOR, CONRR', PO(OH)$_2$ and SO$_3$X, a cationic or non-cationic heterocycle, an aryl or a halogen atom; this hydrocarbon-based chain containing one or more quaternary ammonium radicals;

R and R', which may be identical or different, represent a hydrogen atom or a linear or branched C$_1$–C$_6$ alkyl or C$_2$–C$_6$ alkenyl group, preferably up to C$_4$ inclusive; R and R' may form, with the nitrogen atom to which they are attached, an at least 4-membered heterocycle which may contain at least one additional hetero atom chosen from O, N and S; R and R' or the heterocycle that they form with the nitrogen atom to which they are attached may be substituted with an alkyl, alkoxy, hydroxyalkyl or aminoalkyl radical;

X denotes a hydrogen, an alkali metal or alkaline-earth metal atom or an ammonium group.

A subject of the invention is also a composition for the oxidation dyeing of keratin fibres, and in particular of human keratin fibres such as the hair, characterized in that it contains, in a medium that is suitable for dyeing, as oxidation base, at least one 4,5-diaminopyrazole derivative of formula (I) as defined above, or an addition salt thereof with an acid or a base.

A subject of the invention is also a process for the oxidation dyeing of keratin fibres using such a composition.

As indicated above, the colorations obtained with the oxidation dye composition in accordance with the invention are powerful, particularly bright and chromatic. They in particular produce redder shades that are free of or contain very little blue or yellow. They also have excellent fastness properties with respect to the action of various external agents (light, bad weather, washing, permanent-waving, perspiration and rubbing).

In the context of the present invention, the term "alkyl" means linear or branched radicals containing from 1 to 10 carbon atoms and preferably from 1 to 6 carbon atoms, for example methyl, ethyl, n-propyl, isopropyl, butyl, etc.

"Alkenyl" means a radical containing from 2 to 10 carbon atoms and preferably from 2 to 6 carbon atoms, and containing at least one double bond or one triple bond.

"Heterocycle" denotes 4- to 6-membered aromatic or non-aromatic hydrocarbon-based rings interrupted with at least one hetero atom, preferably from one to three hetero atoms, chosen from O, N and S, and which may be substituted, for example with the substituents as defined above. Mention may be made of rings derived from pyrazole, imidazole, pyridine, piperazine, pyrrolidine, pyrrole, piperidine, imidazolidine, oxazole, oxazoline, etc.

"Aryl" denotes a carbon-based aromatic ring, preferably phenyl.

"Halogen" preferably denotes Cl, Br or I.

"Cationic heterocycle" is, for example, an imidazolium.

The hydrocarbon-based chain B, when it is interrupted with one or more hetero atoms, is preferably interrupted with an oxygen, sulphur and/or nitrogen atom.

According to a first embodiment, B is interrupted with an ammonium radical, for example a tetraalkylammonium radical.

According to this particular case, $R_1$ and $R_2$ are preferably chosen from hydrogen and a methyl or 2-hydroxyethyl group; $R_3$ is preferably chosen from hydrogen and an alkoxy, amino, alkylamino or dialkylamino group; B represents:

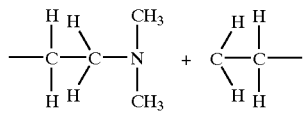

According to one particularly preferred embodiment, $R_1$ to $R_3$ represent hydrogen.

According to another embodiment, B is substituted with a quaternary ammonium radical. For example, B is substituted with a cationic heterocycle.

According to one particularly preferred embodiment, $R_1$ to $R_3$ represent hydrogen.

For example, according to this embodiment, 1,3-bis(4,5-diaminopyrazol-1-yl)propane may be prepared according to the following method:

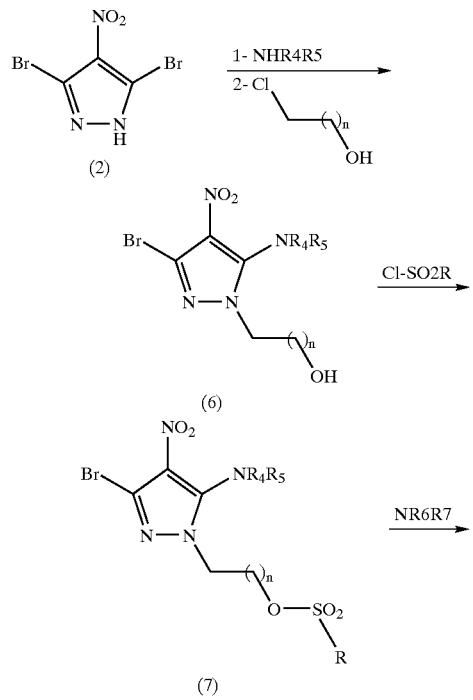

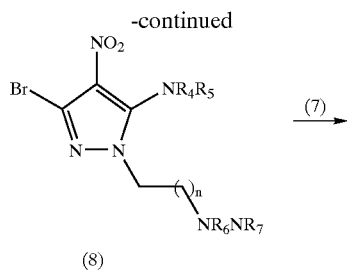

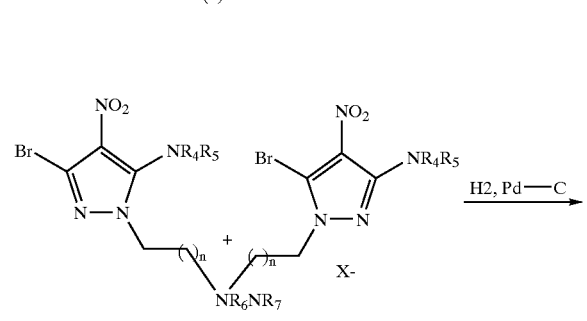

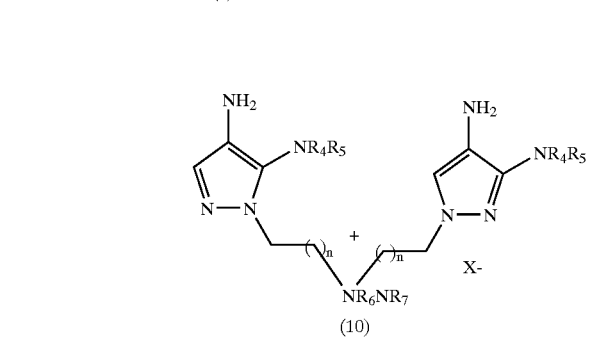

Substitution of the bromine in position 5 with an optionally secondary or tertiary amine of compound 2 leads, in a solvent with a boiling point of between 60 and 180° C., to the 5-amino pyrazole. This product then reacts with a hydroyalkyl chloride in an aprotic solvent to give the pyrazole alkylated in position 1 of formula 6. The alcohol (6) is sulphonylated by reaction with an alkylsulphonyl chloride such as methanesulphonyl chloride, tosyl chloride or triflic acid chloride, to give the sulphonate of formula (7). This electrophile reacts in solvents with a boiling point of between 60 and 140° C. with secondary amines $NHR_6R_7$, in particular at temperatures below 90° C., to give the amino pyrazole of formula (8). This product reacts again with the pyrazole (7) to give the dimer of formula (9), which undergoes a standard reduction reaction of hydrogenation by heterogeneous catalysis or with reductive metals such as zinc, tin or iron to give the expected 4,5-diaminopyrazole dimer.

Another synthetic process consists in reacting the pyrazole (7) with a cyclic or acyclic diamine under the same conditions as those described in the above process, to give the dimer of formula (11) or (13). Alkylation in a solvent with a boiling point of between 60° C. and 150° C. gives the cationic pyrazole dimer, which is then reduced by hydrogenation by heterogeneous catalysis such as Pd/C, Ra—Ni, Pd(OH)₂, or with metals such as zinc, iron or tin, to give the expected cationic pyrazole dimer of formula (12) or (14).

(7) 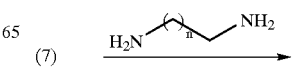

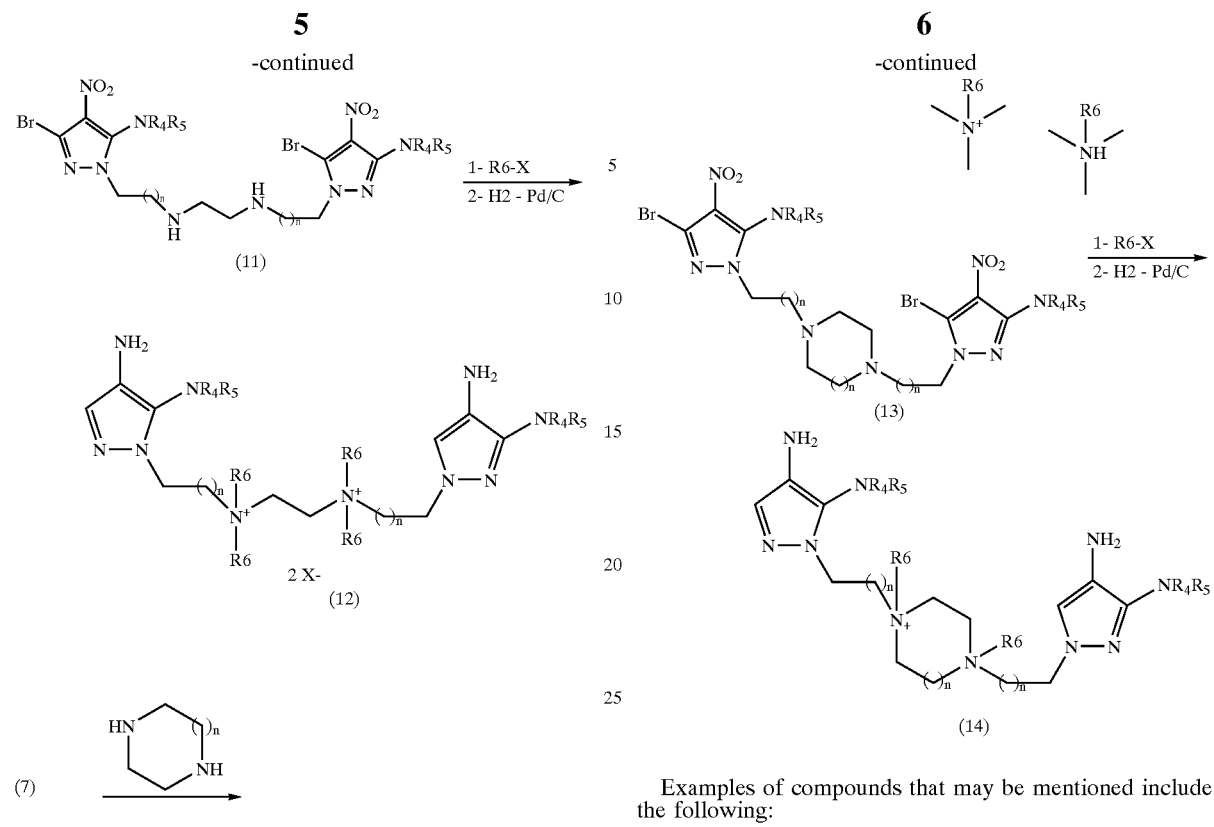
Examples of compounds that may be mentioned include the following:

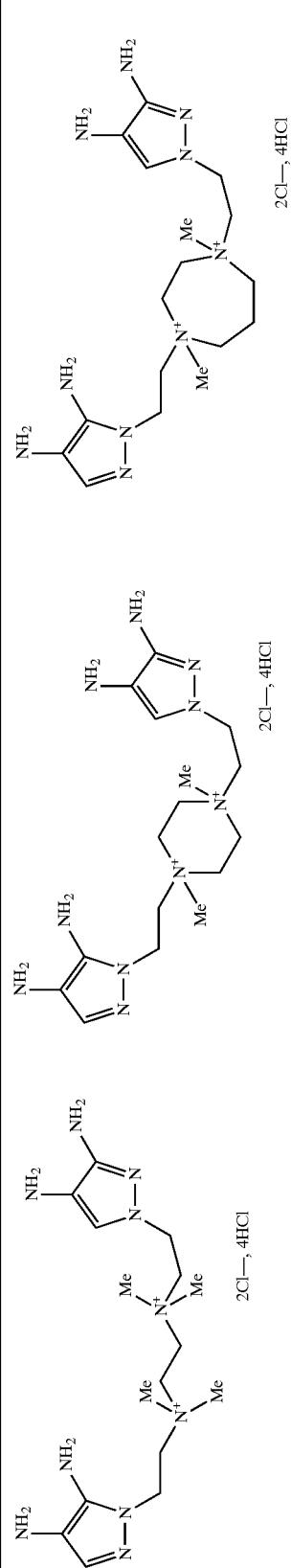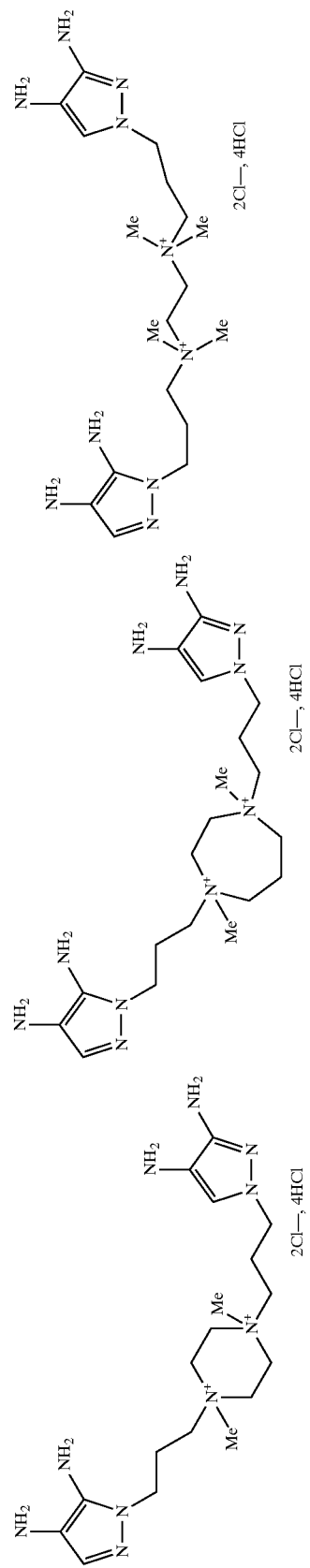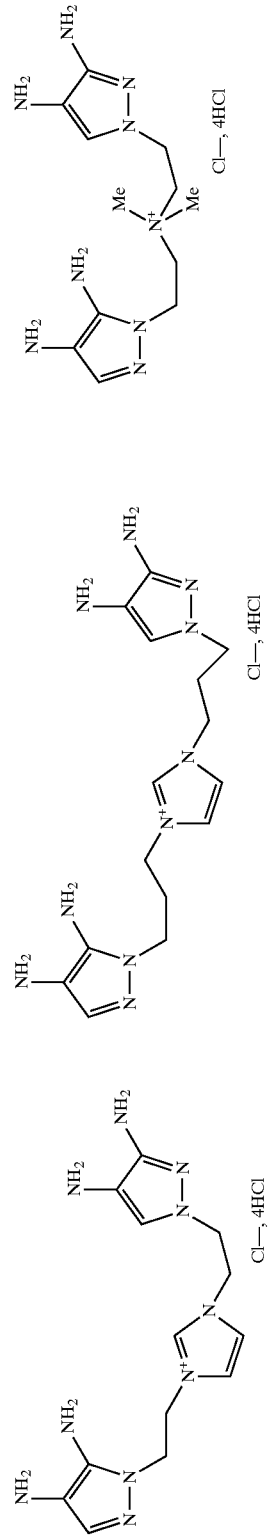

The composition according to the invention generally contains from 0.001% to 10% by weight, preferably from 0.05% to 6% by weight and more preferably from 0.1% to 3% by weight of at least one 4,5-diaminopyrazole derivative of formula (I), or a salt thereof with an acid or a base.

The composition in accordance with the invention may also contain, in addition to the 4,5-diaminopyrazole derivative(s) defined in the invention, at least one additional oxidation base that may be chosen from the oxidation bases conventionally used in oxidation dyeing, and among which mention may be made especially of para-phenylenediamines, bis(phenyl)alkylenediamines, para-aminophenols, ortho-aminophenols and heterocyclic bases other than the 4,5-diaminopyrazoles used in accordance with the invention.

Among the para-phenylenediamines that may be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenyl pyrrolidine, 2-thienyl-para-phenylenediamine and 2-β-hydroxyethylamino-5-aminotoluene, and the addition salts thereof with an acid.

Among the para-phenylenediamines mentioned above that are particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines that can be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)-ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)-ethylenediamine and 1,8-bis(2,5-diaminophenoxy)-3,6-dioxaoctane, and the addition salts thereof with an acid.

Among the para-aminophenols that can be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid.

Among the ortho-aminophenols that can be mentioned, for example, are 2-aminophenol, 2-amino-5-methylphenol, 2-amino-6-methylphenol and 5-acetamido-2-aminophenol, and the addition salts thereof with an acid.

Among the heterocyclic bases, mention may be made, for example, of pyridine derivatives, pyrimidine derivatives and pyrazole derivatives.

Among the pyridine derivatives that may be mentioned are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives that may be mentioned are the compounds described, for example, in German patent DE 2 359 399 or Japanese patents JP 88-169 571; JP 05 163 124; EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylamino-pyrazolo[1,5-a]pyrimidine, and the addition salts thereof with an acid and the tautomeric forms thereof, when a tautomeric equilibrium exists.

Among the pyrazole derivatives that may be mentioned are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

When they are used, these additional oxidation bases preferably represent from 0.0005% to 12% by weight relative to the total weight of the dye composition, and even more preferably from 0.005% to 6% by weight relative to this weight.

The oxidation dye compositions in accordance with the invention may also contain at least one coupler and/or at least one direct dye, especially to modify the shades or to enrich them with glints.

The couplers that may be used in the oxidation dye compositions in accordance with the invention may be chosen from the couplers conventionally used in oxidation dyeing, and among which mention may be made especially of meta-phenylenediamines, meta-aminophenols, meta-diphenols, mono- or polyhydroxylated naphthalene derivatives and heterocyclic couplers such as, for example, indole or pyridine derivatives, and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxy-benzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene and the addition salts thereof.

When they are present, these couplers especially represent from 0.0001% to 10% of the total weight of the dye composition, preferably from 0.005% to 5% by weight and even more preferably from 0.1% to 3% of this weight.

Direct dyes that may be mentioned include nitrobenzene dyes, cationic direct dyes, azo direct dyes and methine direct dyes.

In general, the addition salts with an acid that may be used in the dye compositions of the invention (oxidation bases and couplers) are chosen especially from the hydrochlorides, hydrobromides, sulphates, tartrates, lactates and acetates. The addition salts with a base are especially those obtained with sodium hydroxide, potassium hydroxide, aqueous ammonia, amines or alkanolamines.

The medium that is suitable for dyeing (or support) used according to the invention consists of water or of a mixture of water and at least one organic solvent chosen from $C_1$–$C_4$ lower alkanols, polyols and polyol ethers, aromatic alcohols, similar products and mixtures thereof.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic or amphoteric associative polymeric thickeners, antioxidants, penetration agents, sequestering agents, fragrances, buffers, dispersants, conditioners such as, for example, silicones, which may or may not be volatile or modified, film-forming agents, ceramides, preserving agents and opacifiers.

The pH of the dye composition in accordance with the invention is generally between about 3 and 12 and preferably between about 5 and 11. It may be adjusted to the desired value using acidifying or basifying agents usually used in the dyeing of keratin fibres, or alternatively using standard buffer systems.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (III) below:

(III)

in which W is a propylene residue which is unsubstituted or substituted with a hydroxyl group or a $C_1$–$C_4$ alkyl radical; $R_6$, $R_7$, $R_8$ and $R_9$, which may be identical or different, represent a hydrogen atom, a $C_1$–$C_4$ alkyl radical or a $C_1$–$C_4$ hydroxyalkyl radical.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for dyeing keratin fibres, and in particular human keratin fibres such as the hair, using the dye composition as defined above.

According to this process, at least one dye composition as defined above is applied to the fibres, for a time that is sufficient to develop the desired coloration, either in air or using an oxidizing agent. The dye composition may optionally contain oxidation catalysts, in order to accelerate the oxidation process.

According to a first embodiment of the process of the invention, the fibres may be dyed without adding an oxidizing agent, merely by contact with atmospheric oxygen.

According to a second embodiment of the process of the invention, at least one dye composition as defined above is applied to the fibres, the colour being developed at acidic, neutral or alkaline pH using an oxidizing agent that is added just at the time of use to the dye composition, or that is present in an oxidizing composition applied simultaneously or sequentially in a separate manner.

According to this second embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes, preferably 5 to 30 minutes, after which the fibres are rinsed, washed with shampoo, rinsed again and dried.

The oxidizing agent present in the oxidizing composition as defined above may be chosen from the oxidizing agents conventionally used for the oxidation dyeing of keratin fibres, and among which mention may be made of hydrogen peroxide, urea peroxide, alkali metal bromates, persalts such as perborates and persulphates, peracids, and oxidase enzymes, among which mention may be made of peroxidases, 2-electron oxidoreductases such as uricases, and 4-electron oxygenases, for instance laccases. Hydrogen peroxide is particularly preferred.

The pH of the oxidizing composition containing the oxidizing agent as defined above is such that, after mixing with the dye composition, the pH of the resultant composition applied to the keratin fibres preferably varies between 3 and 12, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams, gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains an oxidizing composition. These devices can be equipped with a means for delivering the desired mixture onto the hair, such as the devices described in patent FR-2 586 913 in the name of the Applicant.

What is claimed is:

1. A compound chosen from 4,5-diaminopyrazole derivative compounds of formula (I) and the addition salts thereof with a physiologically acceptable acid or base:

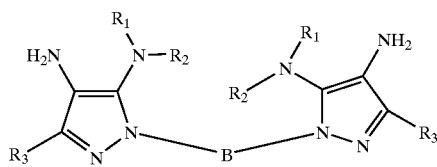

(I)

wherein $R_1$, $R_2$, and $R_3$, which may be identical or different, are chosen from a hydrogen atom; linear and branched alkyl radicals and linear and branched alkenyl radicals wherein the alkyl and alkenyl radicals may be substituted with at least one group chosen from OR, NRR', SR, SOR, $SO_2R$, COOR, CONRR', $PO(OH)_2$ and $SO_3X$ groups, cationic and non-cationic heterocycles, aryl groups and halogen atoms; $R_1$ and $R_2$ together may form a heterocycle comprising at least four atoms including the nitrogen atom to which they are attached;

$R_3$ is chosen from alkoxy, amino, alkylamino and dialkylamino radicals;

B is chosen from linear and branched, saturated and unsaturated $C_1$–$C_{14}$ hydrocarbon-based chains, which may comprise at least one bond chosen from double and triple bonds and which may be substituted with at least one group chosen from OR. NRR', SR, SOR, $SO_2R$, COOR, CONRR', $PO(OH)_2$ and $SO_3X$ groups, cationic and non-cationic heterocycles, aryl groups and halogen atoms; this hydrocarbon-based chain comprising at least one quaternary ammonium radical;

R and R', which may be identical or different, are chosen from a hydrogen atom, linear and branched $C_1$–$C_6$ alkyl groups and linear and branched $C_2$–$C_6$ alkenyl groups, R and R' may form, with the nitrogen atom to which they are attached, an at least 4-membered heterocycle which may comprise at least one additional hetero atom chosen from O, N and S; R and R' or the heterocycle that they form with the nitrogen atom to which they are attached may be substituted with a radical chosen from alkyl, alkoxy, hydroxyalkyl and aminoalkyl radicals;

X is chosen from a hydrogen atom, alkali metal atoms, alkaline-earth metal atoms and ammonium groups.

2. The compound according to claim 1, wherein R and R' are chosen from a hydrogen atom, linear and branched $C_1$–$C_4$ alkyl groups and linear branched $C_1$–$C_4$ alkenyl groups.

3. The compound according to claim 1, wherein B is interrupted with a quaternary ammonium radical.

4. The compound according to claim 1, wherein B is interrupted with a tetraalkylammonium radical.

5. The compound according to claim 1, wherein B is substituted with at least one ammonium radical.

6. The compound according to claim 1, wherein B is substituted with at least one cationic heterocycle.

7. The compound according to claim 1, wherein $R_1$ and $R_2$, which may be identical or different, are chosen from a hydrogen atom, a methyl group, and a 2-hydroxyethyl group; $R_3$ is chosen from a hydrogen atom and from alkoxy, amino, alkylamino and dialkylamino groups; and B is:

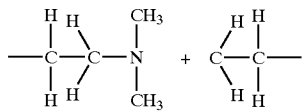

8. The compound according to claim 1, wherein the compound is chosen from 4,5-diaminopyrazole derivatives of the following formulae:

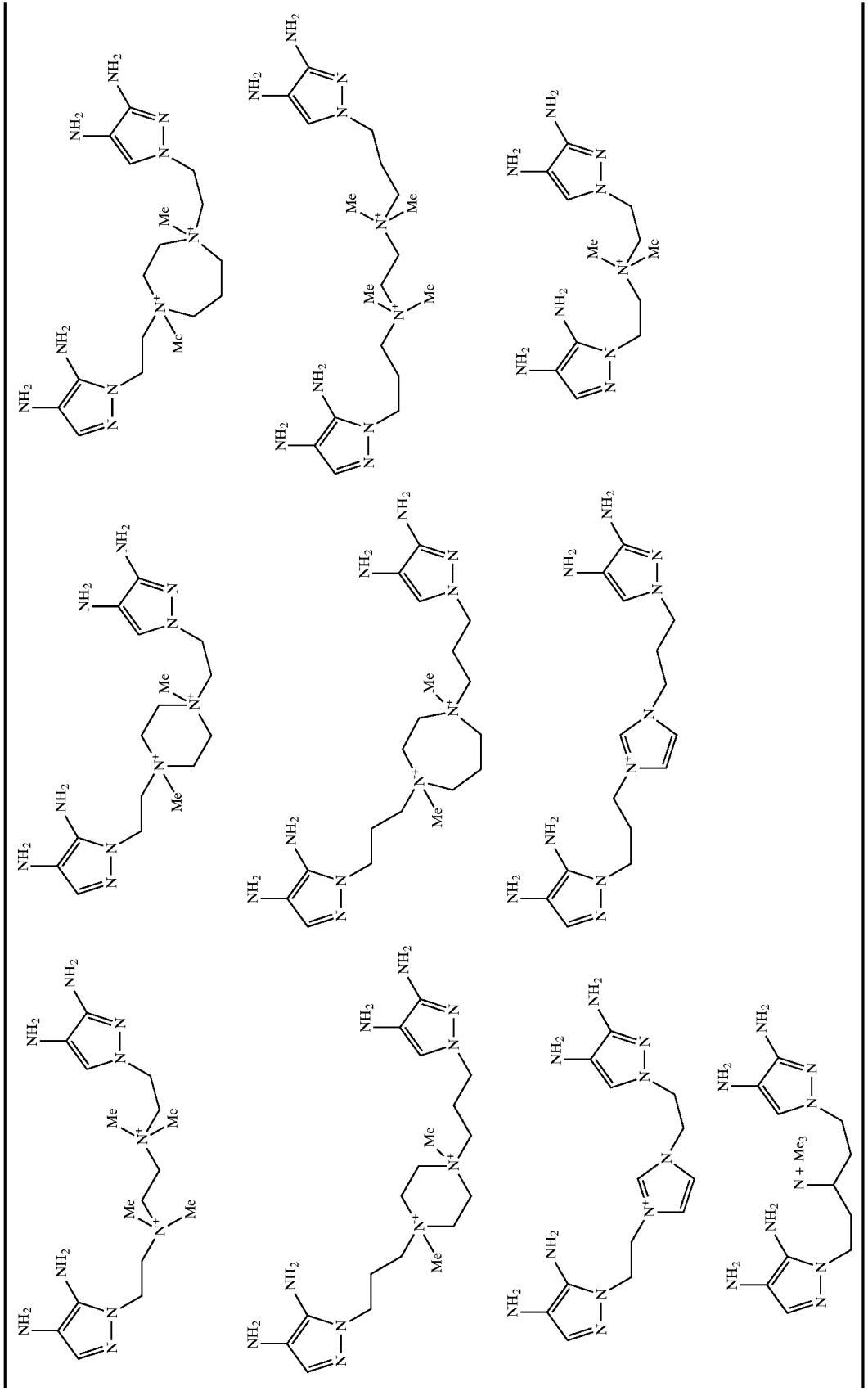

and the addition salts thereof with an acid or a base.

9. The compound according to claim 1, wherein the physiologically acceptable acid salts addition are chosen from hydrochlorides, hydrobromides, sulphates, tartrates, lactates and acetates, and the physiologically acceptable base addition salts are chosen from sodium hydroxide, potassium hydroxide, ammonia, amines and alkanolamines.

10. A composition for the oxidative dyeing of keratin fibers, comprising, in a medium suitable for dyeing, as oxidation base, at least one 4,5-diaminopyrazole derivative chosen from compounds of formula (I) and the addition salts thereof with a physiologically acceptable acid or base:

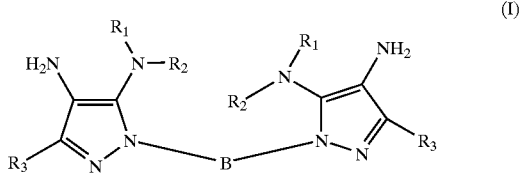

(I)

wherein $R_1$, $R_2$, and $R_3$, which may be identical or different, are chosen from a hydrogen atom; linear and branched alkyl radicals and linear and branched alkenyl radicals wherein the alkyl and alkenyl radicals may be substituted with at least one group chosen from OR, NRR', SR, SOR, $SO_2R$, COOR, CONRR', $PO(OH)_2$ and $SO_3X$ groups, cationic and non-cationic heterocycles, aryl groups and halogen atoms; $R_1$ and $R_2$ together may form a heterocycle comprising at least four atoms including the nitrogen atom to which they are attached;

$R_3$ is chosen from alkoxy, amino, alkylamino and dialkylamino radicals;

B is chosen from linear and branched, saturated and unsaturated $C_1$–$C_{14}$ hydrocarbon-based chains, which may comprise at least one bond chosen from double and triple bonds and which may be substituted with at least one group chosen from OR, NRR', SR, SOR, $SO_2R$, COOR, CONRR', $PO(OH)_2$ and $SO_3X$ groups, cationic and non-cationic heterocycles, aryl groups and halogen atoms; this hydrocarbon-based chain comprising at least one quaternary ammonium radical;

R and R', which may be identical or different, are chosen from a hydrogen atom, linear and branched $C_1$–$C_6$ alkyl groups and linear and branched $C_2$–$C_6$ alkenyl groups, R and R' may form, with the nitrogen atom to which they are attached, an at least 4-membered heterocycle which may comprise at least one additional hetero atom chosen from O, N and S; R and R' or the heterocycle that they form with the nitrogen atom to which they are attached may be substituted with a radical chosen from alkyl, alkoxy, hydroxyalkyl and aminoalkyl radicals;

X is chosen from a hydrogen atom, alkali metal atoms, alkaline-earth metal atoms and ammonium groups.

11. The composition according to claim 10, wherein the at least one 4,5-diaminopyrazole derivative is present in an amount ranging from 0.001% to 10% by weight, relative to the total weight of the composition.

12. The composition according to claim 10, wherein the medium that is suitable for dyeing comprises water or a mixture of water and at least one organic solvent chosen from $C_1$–$C_4$ lower alkanols, polyols and polyethers, and aromatic alcohols.

13. The composition according to claim 10, wherein the composition has a pH ranging from 3 to 12.

14. The composition according to claim 10, further comprising at least one additional oxidation base chosen from para-phenylenediamines, bis(phenyl)alkylenediamines, para-aminophenols, ortho-aminophenols and heterocyclic bases other than the 4,5-diaminopyrazole derivatives of formula (I), and the acid addition salts thereof.

15. The composition according to claim 14, wherein at least one additional oxidation base is present in an amount ranging from 0.0005% to 12% by weight, relative to the total weight of the composition.

16. The composition according to claim 10, further comprising at least one coupler chosen from meta-phenylenediamines, meta-aminophenols, meta-diphenols, mono- or polyhydroxylated naphthalene derivatives and heterocyclic couplers, and the addition salts thereof.

17. The composition according to claim 16, wherein at least one coupler is present in an amount ranging from 0.0001% to 10% by weight, relative to the total weight of the composition.

18. The composition according to claim 10, further comprising at least one direct dye chosen from nitrobenzene dyes, cationic direct dyes, azo direct dyes and methine direct dyes.

19. A process for dyeing keratin fibers, comprising applying to the keratin fibers for a time sufficient to develop the desired coloration, either in air or using an oxidizing agent, optionally in the presence of at least one oxidation catalyst, a composition for the oxidative dyeing of keratin fibers, comprising in a medium suitable for dyeing, as oxidation base at least one 4,5-diaminopyrazole derivative chosen from compounds of formula (I) and the addition salts thereof with a physiologically acceptable acid or base:

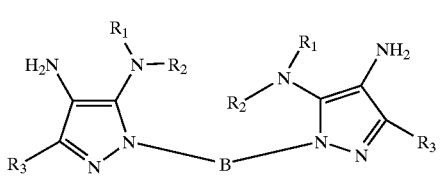

(I)

wherein $R_1$, $R_2$, and $R_3$, which may be identical or different, are chosen from a hydrogen atom; linear and branched alkyl radicals and linear and branched alkenyl radicals wherein the alkyl and alkenyl radicals may be substituted with at least one group chosen from OR, NRR', SR, SOR, $SO_2R$, COOR, CONRR', $PO(OH)_2$ and $SO_3X$ groups, cationic and non-cationic heterocycles, aryl groups and halogen atoms; $R_1$ and $R_2$ together may form a heterocycle comprising at least four atoms including the nitrogen atom to which they are attached;

$R_3$ is chosen from alkoxy, amino, alkylamino and dialkylamino radicals;

B is chosen from linear and branched, saturated and unsaturated $C_1$–$C_{14}$ hydrocarbon-based chains, which may comprise at least one bond chosen from double and triple bonds and which may be substituted with at least one group chosen from OR, NRR', SR, SOR, $SO_2R$, COOR, CONRR', $PO(OH)_2$ and $SO_3X$ groups, cationic and non-cationic heterocycles, aryl groups and halogen atoms; this hydrocarbon-based chain comprising at least one quaternary ammonium radical;

R and R', which may be identical or different, are chosen from a hydrogen atom, linear and branched $C_1$–$C_6$ alkyl groups and linear and branched $C_2$–$C_6$ alkenyl groups, R and R' may form, with the nitrogen atom to which they are attached, an at least 4-membered heterocycle which may comprise at least one additional hetero atom chosen from O, N and S; R and R' or the heterocycle that they form with the nitrogen atom to which they are attached may be substituted with a radical chosen from alkyl, alkoxy, hydroxyalkyl and aminoalkyl radicals;

X is chosen from a hydrogen atom, alkali metal atoms, alkaline-earth metal atoms and ammonium groups.

20. The process according to claim 19, the coloration is developed by contact with atmospheric oxygen.

21. The process according to claim 19, wherein the color is developed at acidic, neutral or alkaline pH using an oxidizing agent that is added just at the time of use to the dye composition, or that is present in an oxidizing composition applied simultaneously or sequentially in a separate manner.

22. The process according to claim 21, wherein the oxidizing agent is chosen from hydrogen peroxide, urea peroxide, alkali metal bromates, persalts peracids and oxidase enzymes.

23. The process according to claim 22, wherein said persalts are chosen from perborates and persulphates.

24. A multi-compartment dyeing device, comprising at least one first compartment comprising a composition for the oxidative dyeing of keratin fibers, comprising, in a medium suitable for dyeing, as oxidation base, at least one 4,5-diaminopyrazole derivative chosen from compounds of formula (I) and the addition salts thereof with a physiologically acceptable acid or base:

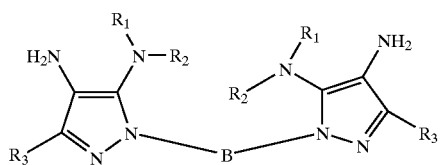

(I)

wherein

R$_1$, R$_2$, and R$_3$, which may be identical or different, are chosen from a hydrogen atom; linear and branched alkyl radicals and linear and branched alkenyl radicals wherein the alkyl and alkenyl radicals may be substituted with at least one group chosen from OR, NRR', SR, SOR, SO$_2$R, COOR, CONRR', PO(OH)$_2$ and SO$_3$X groups, cationic and non-cationic heterocycles, aryl groups and halogen atoms; R$_1$ and R$_2$ together may form a heterocycle comprising at least four atoms including the nitrogen atom to which they are attached;

R$_3$ is chosen from alkoxy, amino, alkylamino and dialkylamino radicals;

B is chosen from linear and branched, saturated and unsaturated C$_1$–C$_{14}$ hydrocarbon-based chains, which may comprise at least one bond chosen from double and triple bonds and which may be substituted with at least one group chosen from OR, NRR', SR, SOR, SO$_2$R, COOR, CONRR', PO(OH)$_2$ and SO$_3$X groups, cationic and non-cationic heterocycles, aryl groups and halogen atoms; this hydrocarbon-based chain comprising at least one quaternary ammonium radical;

R and R', which may be identical or different, are chosen from a hydrogen atom, linear and branched C$_1$–C$_6$ alkyl groups and linear and branched C$_2$–C$_6$ alkenyl groups, R and R' may form, with the nitrogen atom to which they are attached, an at least 4-membered heterocycle which may comprise at least one additional hetero atom chosen from O, N and S; R and R' or the heterocycle that they form with the nitrogen atom to which they are attached may be substituted with a radical chosen from alkyl, alkoxy, hydroxyalkyl and aminoalkyl radicals;

X is chosen from a hydrogen atom, alkali metal atoms, alkaline-earth metal atoms and ammonium groups, and comprising at least another compartment comprising an oxidizing composition.

25. A colored product obtained by oxidative condensation of a composition for the oxidative dyeing of keratin fibers, said composition comprising, in a medium suitable for dyeing, as oxidation base, at least one 4,5-diaminopyrazole derivative chosen from compounds of formula (I) and the addition salts thereof with a physiologically acceptable acid or base:

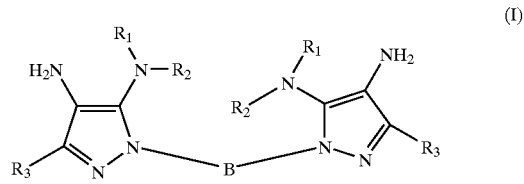

(I)

wherein

R$_1$, R$_2$, and R$_3$, which may be identical or different, are chosen from a hydrogen atom; linear and branched alkyl radicals and linear and branched alkenyl radicals wherein the alkyl and alkenyl radicals may be substituted with at least one group chosen from OR, NRR', SR, SOR, SO$_2$R, COOR, CONRR', PO(OH)$_2$ and SO$_3$X groups, cationic and non-cationic heterocycles, aryl groups and halogen atoms; R$_1$ and R$_2$ together may form a heterocycle comprising at least four atoms including the nitrogen atom to which they are attached;

R$_3$ is chosen from alkoxy, amino, alkylamino and dialkylamino radicals;

B is chosen from linear and branched, saturated and unsaturated C$_1$–C$_{14}$ hydrocarbon-based chains, which may comprise at least one bond chosen from double and triple bonds and which may be substituted with at least one group chosen from OR, NRR', SR, SOR, SO$_2$R, COOR, CONRR', PO(OH)$_2$ and SO$_3$X groups, cationic and non-cationic heterocycles, aryl groups and halogen atoms; this hydrocarbon-based chain comprising at least one quaternary ammonium radical;

R and R', which may be identical or different, are chosen from a hydrogen atom, linear and branched C$_1$–C$_6$ alkyl groups and linear and branched C$_2$–C$_6$ alkenyl groups. R and R' together may form, with the nitrogen atom to which they are attached, an at least 4-membered heterocycle which may comprise at least one additional hetero atom chosen from O, N and S; R and R' or the heterocycle that they form with the nitrogen atom to which they are attached may be substituted with a radical chosen from alkyl, alkoxy, hydroxyalkyl and aminoalkyl radicals;

X is chosen from a hydrogen atom, alkali metal atoms, alkaline-earth metal atoms and ammonium groups.

* * * * *

UNITED STATES PATENT AND TRADEMARK OFFICE
CERTIFICATE OF CORRECTION

PATENT NO. : 6,939,382 B2  Page 1 of 1
DATED : September 6, 2005
INVENTOR(S) : Thilo Fessmann and Eric Terraova It is certified that error appears in the above-identified patent and that said Letters Patent is hereby corrected as shown below:

<u>Title page,</u>
Item [54], Title, "4, 5-DIAMINOPYRAZOLE" should read -- 4,5-DIAMINOPYRAZOLE --.
Item [75], Inventors, "Aulnay solus Bois" should read -- Aulnay Sous Bois --.
Item [57], ABSTRACT,
Line 1, "present, invention" should read -- present invention --.

<u>Column 14,</u>
Line 2, "OR." should read -- OR, --.
Line 23, "linear branched" should read -- linear and branched --.

<u>Column 17,</u>
Line 3, "salts addition" should read -- addition salts --.

<u>Column 19,</u>
Line 9, "claim 19, the" should read -- claim 19, wherein the --.
Line 18, "persalts peracids" should read -- persalts, peracids --.

<u>Column 20,</u>
Line 53, "groups." should read -- groups, --.

Signed and Sealed this

Fourth Day of April, 2006

JON W. DUDAS
*Director of the United States Patent and Trademark Office*